United States Patent
Hord et al.

[11] Patent Number: 6,070,451
[45] Date of Patent: Jun. 6, 2000

[54] PROCESS AND APPARATUS FOR TESTING OF GAS CYLINDERS

[75] Inventors: W. D. Hord; David Norboge, both of Bellville, Tex.

[73] Assignee: Western International Gas and Cylinders, Inc., Bellville, Tex.

[21] Appl. No.: 08/833,383

[22] Filed: Apr. 4, 1997

[51] Int. Cl.[7] .............................. G01M 3/02; G01B 7/54
[52] U.S. Cl. .................... 73/37; 73/49.5; 364/551.01
[58] Field of Search ................... 73/37, 40, 49.5, 73/49.2; 364/551.01, 579, 580

[56] References Cited

U.S. PATENT DOCUMENTS

| | | | |
|---|---|---|---|
| 3,534,587 | 10/1970 | Grenci | 73/49.8 |
| 4,002,054 | 1/1977 | Grenci | 73/37 |
| 4,419,884 | 12/1983 | Grenci et al. | 73/49.8 |
| 4,528,840 | 7/1985 | Wass | 73/37 |
| 4,873,654 | 10/1989 | Alexander et al. | 364/551.01 |
| 4,893,494 | 1/1990 | Hart | 73/37 |
| 5,036,707 | 8/1991 | Paciej et al. | 73/637 |
| 5,295,392 | 3/1994 | Hensel et al. | 73/37 |

*Primary Examiner*—Hezron Williams
*Assistant Examiner*—Jay L. Politzer
*Attorney, Agent, or Firm*—Thomason, Moser & Patterson, LLP

[57] ABSTRACT

An method and apparatus for testing of gas cylinders which combines a cylinder preparation station, a cylinder test station, a system controller for controlling data entry and cylinder testing, the system controller comprising a data entry device located near the cylinder preparation station, a test control device located near the cylinder station, and a memory comprising a cylinder test condition database and a cylinder test database. The apparatus is programmed to conduct a process comprising the steps of entering data from a cylinder into the data entry device, selecting test conditions for the cylinder from the cylinder test condition database, testing the cylinder using the test conditions, and adding test results for the cylinder to the cylinder test results database.

20 Claims, 4 Drawing Sheets

PROCESS AND APPARATUS FOR TESTING OF GAS CYLINDERS

BACKGROUND OF THE INVENTION

This invention relates to testing or reconditioning of gas cylinders. More specifically, the invention relates to a process and apparatus for testing the gas cylinders for structural integrity prior to reconditioning of the cylinders.

Industrial gases such as nitrogen, oxygen, and helium are typically supplied in metal cylinders which are refilled many times. Department of Transportation regulations require that each gas cylinder must have a record of successful testing for structural integrity to be refilled using normal procedures. Approved cylinder test methods include hydrostatic testing and ultrasonic testing. Hydrostatic testing typically includes measurement of permanent expansion and elastic expansion. Cylinders which fail a visual inspection, exceed an acceptable permanent expansion, or have unacceptable defects must not be refilled. Cylinders which are acceptable except for inadequate elastic expansion can be used only at a reduced pressure which is typically the pressure limit stamped on the cylinder.

Reconditioning of empty gas cylinders generally involves removing the cylinder valve, inspecting and testing the cylinder, cleaning, drying, and repainting the cylinder, and replacing a cylinder valve on the reconditioned cylinder. Inspection and testing of gas cylinders is usually the bottleneck in the reconditioning process since test conditions and results are determined and documented for each cylinder.

Hydrostatic testing of the gas cylinders was improved by a computerized hydrostatic test station marketed by Galiso, Inc. However, the hydrostatic test stations place much responsibility on a single operator and essentially causes the operator to be the bottleneck in a process that is primarily constrained by the ability of the operator to enter data.

It is an object of the present invention to significantly increase the number of gas cylinders which can be tested for structural integrity by enhancing data entry. Successful debottlenecking of the cylinder testing process will further debottleneck reconditioning of used gas cylinders.

SUMMARY OF THE INVENTION

The present invention provides a method and apparatus for testing of gas cylinders which significantly improves upon available test equipment and methods used during reconditioning of the cylinders. The apparatus comprises a cylinder preparation station, a cylinder test station, a system controller for controlling data entry and cylinder testing, the system controller including a data entry device located near the cylinder preparation station, a test control device located near the cylinder test station, and a memory comprising a cylinder test condition database and a cylinder test results database. The apparatus is programmed to conduct a process comprising the steps of entering data from a cylinder into the data entry device, selecting test conditions for the cylinder from the cylinder test condition database, adding the test conditions to the cylinder test results database, testing the cylinder using the test conditions, and adding test results for the cylinder to the cylinder test results database.

DESCRIPTION OF THE DRAWINGS

So that the above recited features, advantages and objects of the present invention can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE INVENTION

The present invention provides a gas cylinder testing method and apparatus which can be included in a cylinder testing or reconditioning facility. The apparatus comprises a cylinder preparation station, a cylinder test station, and a system controller for controlling data entry and cylinder testing. The system controller comprises a data entry device located near the cylinder preparation station and a test control device located near the cylinder test station. A memory is coupled to the system controller, the memory comprising a cylinder test condition database and a cylinder test results database.

Figure 1:
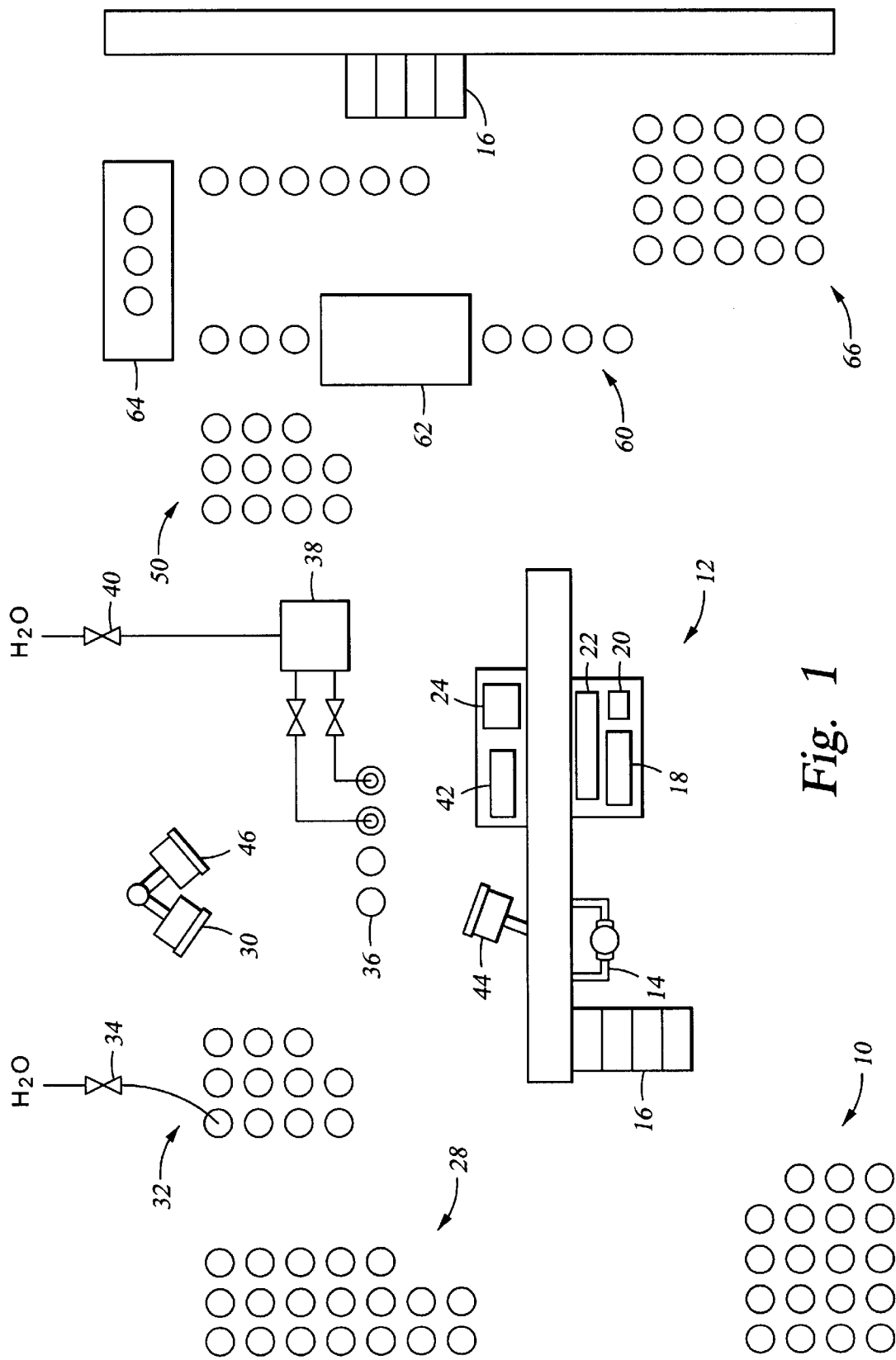
FIG. 1 is a schematic diagram of a preferred cylinder reconditioning facility which includes hydrostatic testing of the cylinders and a computer controller which provides multiple data entry and data monitoring.

Referring to FIG. 1, a preferred gas cylinder reconditioning facility includes a hydrostatic testing apparatus which is constructed and operated according to the present invention. Empty gas cylinders are placed in a receiving area 10 near a cylinder preparation station 12. The cylinder preparation station 12 includes cylinder clamps 14 for holding one or more cylinders while valves are removed and sequentially placed in a segmented valve bin 16. The cylinder valves are removed to facilitate hydrostatic testing as well as reconditioning of the cylinders. Ultrasonic testing does not require removal of the cylinder valve although valve removal may be part of the reconditioning process. Information contained on the cylinders is read by a first operator and entered in a data entry device such as a keyboard 18, a mouse 20, or a touch screen on a first computer monitor 22 which is preferably mounted on a wall adjacent the cylinder clamps 14. Some of the important information is stamped on the cylinder by the cylinder manufacturer and may be covered by paint or old labels that are removed after all relevant information on the old labels has been entered.

Entry of the cylinder information is facilitated by a cylinder code table which allows the first operator to use readily available information such as cylinder dimensions to identify standard cylinders and enter standard cylinder information by selecting the correct cylinder code. The code table can be updated to include additional types of cylinders which may be frequently tested. The entered cylinder information for each cylinder is used to search a cylinder test condition database to identify the appropriate test conditions for the cylinder. Thus, any variation in a standard cylinder which requires a variation in the cylinder testing also requires selection of the variation in the code table to facilitate rapid determination of the correct cylinder test conditions. The cylinder data and test conditions are stored in a cylinder test results database in a computer processing unit (CPU) 24.

The first operator visually inspects each cylinder, decides whether the cylinder is acceptable for reconditioning, and enters the decision along with the cylinder data. After cylinder preparation and data entry, the cylinders are moved in sequence to a cylinder staging area 28, usually by the first operator.

A second computer monitor 30 is mounted near a cylinder test preparation area 32 and displays the sequence of cylinders entered in the cylinder test results database. The cylinders are moved from the staging area 28 to the test preparation area 32, usually by a second operator, while maintaining the cylinders in the sequence dictated by the entry of data in the cylinder test results database as shown on the second monitor 30. In the test preparation area 32 the cylinders are aligned in one or more columns, depending on the number of separate testing units, and filled with water from one or more water sources 34. The cylinders are then lifted one at a time into one or more cylinder test jackets 36 wherein the cylinders are hydrostatically tested using a hydrostatic test unit 38. Hydrostatic test units are commercially available from several manufacturers including GALISO, Inc. The test unit 38 pressurizes the cylinders with water from a water source 40 to a test pressure as described below. The test unit 38 is preferably linked to the CPU 24 which can assist in running the correct test conditions. The second operator interacts with the test unit 38 using a keyboard 42 and two identical displays 44, 46.

The cylinder test unit 38 records the test pressure and the displacement of water from the test jacket 36 to calculate permanent expansion and elastic expansion for the cylinder. Hydrostatic test results are automatically added to the cylinder test results database along with an indication of whether the cylinder passed or failed the test method. The test unit 38 stops when a cylinder fails a test and prompts the operator to mark the failed cylinders showing which test was failed. The cylinders which passed the test are then moved to a final test staging area 50, usually by a third operator, in preparation for re-valving.

The cylinders are preferably cleaned following hydrostatic testing and visually inspected again by the third operator who marks any additional failed cylinders. The first operator reviews available data for failed or aborted cylinders and decides whether re-testing may result in acceptance of the cylinder or whether the cylinder should be discarded. Any of the test operators can submit comments which may assist in re-test decisions. Retests are expedited to maintain the appropriate cylinder sequence.

The cylinders which passed the test are optionally painted and then re-valved. Each cylinder to be painted is lifted onto a cylinder conveyor 60 which passes the cylinders through an oven drier 62 and a paint shed 64 where the cylinders which are spray painted. The painted cylinders dry while on the conveyor and are thin refitted with the valve originally removed from the cylinder using the segmented valve bin 16 that was originally located at the cylinder preparation station 12. The cylinders remain in sequence in a final shipping area 66 where print-outs of the cylinder database are used to ship each cylinder to its owner along with documents showing the test results for retention by the cylinder owners.

The CPU 24, data entry devices 18, 20, 22, 42, and various monitors 22, 30, 44, 46, are part of a computer system controller 70 which executes system control software stored in a memory which in the preferred embodiment includes a hard disk drive. The system controller 70 controls all of the activities of the hydrostatic testing of the gas cylinders and is an integral part of the testing apparatus. The system controller 70 includes a hard disk drive, a floppy disk drive, and a motherboard. The motherboard comprises analog and digital input/output boards, and operator interface boards.

The system controller 70 operates under the control of computer programs stored on the hard disk drive. The computer program dictates the sequence of process steps and the parameters of a particular process step.

The process steps discussed below can be implemented using a computer program product that runs on, for example, the CPU 24 using a WINDOWS 95 environment. However, the computer program code can be written in any conventional computer readable programming language such as for example 68000 assembly language, C, C+, C++, or Pascal. Suitable program code is entered into a single file, or multiple files, using a conventional test editor, and stored or embodied in a computer usable medium, such as a memory system of the computer. If the entered code text is in a high level language, the code is compiled, and the resultant compiler code is then linked with a object code of precompiled windows library routines. To execute the linked compiled object code, the system user invokes the object code, causing the computer system to load the code in memory, from which the CPU reads and executes the code to perform the tasks identified in the program.

The present invention generally provides a process for testing of gas cylinders, comprising the steps of entering data from a cylinder into a data entry device, selecting test conditions for the cylinder for a hydrostatic test condition database, adding the test conditions to a cylinder test results database stored in the computer memory, testing the cylinder using the test conditions, and adding the hydrostatic test results to the cylinder test results database.

The cylinder test condition database simplifies data entry by storing test conditions for each type and size of gas cylinder so that the operator needs to enter only a sufficient number of coded characters to distinguish the various types and sizes of cylinders. The operator further enters the cylinder serial number and ownership information which may be on a label or marked directly on the cylinder when a shipment of cylinders is received without an owner's label. Successful entry of data in each field for a cylinder results in retrieval of the test conditions for that cylinder. Both the cylinder data and the test conditions are added to the cylinder test results database. The first operator can add new types of cylinders to the test condition database and assign new codes for subsequent data entry whenever a new cylinder type is encountered and test conditions can be identified.

The cylinder test results database is accessible by all data entry devices, all monitors, and one or more printers. Cylinder owners are responsible for retaining documented test results and the database is not intended for long term storage of cylinder test data. After suitable documentation is created for a cylinder test, the entry is eventually deleted. Documentation of failed or aborted tests is as important as documenting successful tests.

The computer readable programming code for the apparatus shown in FIG. 1 is best described by reference to program flow diagrams shown in FIGS. 2–4. Persons skilled in computer programming can write readable program code which implements the steps shown in the flow diagrams.

Figure 2:
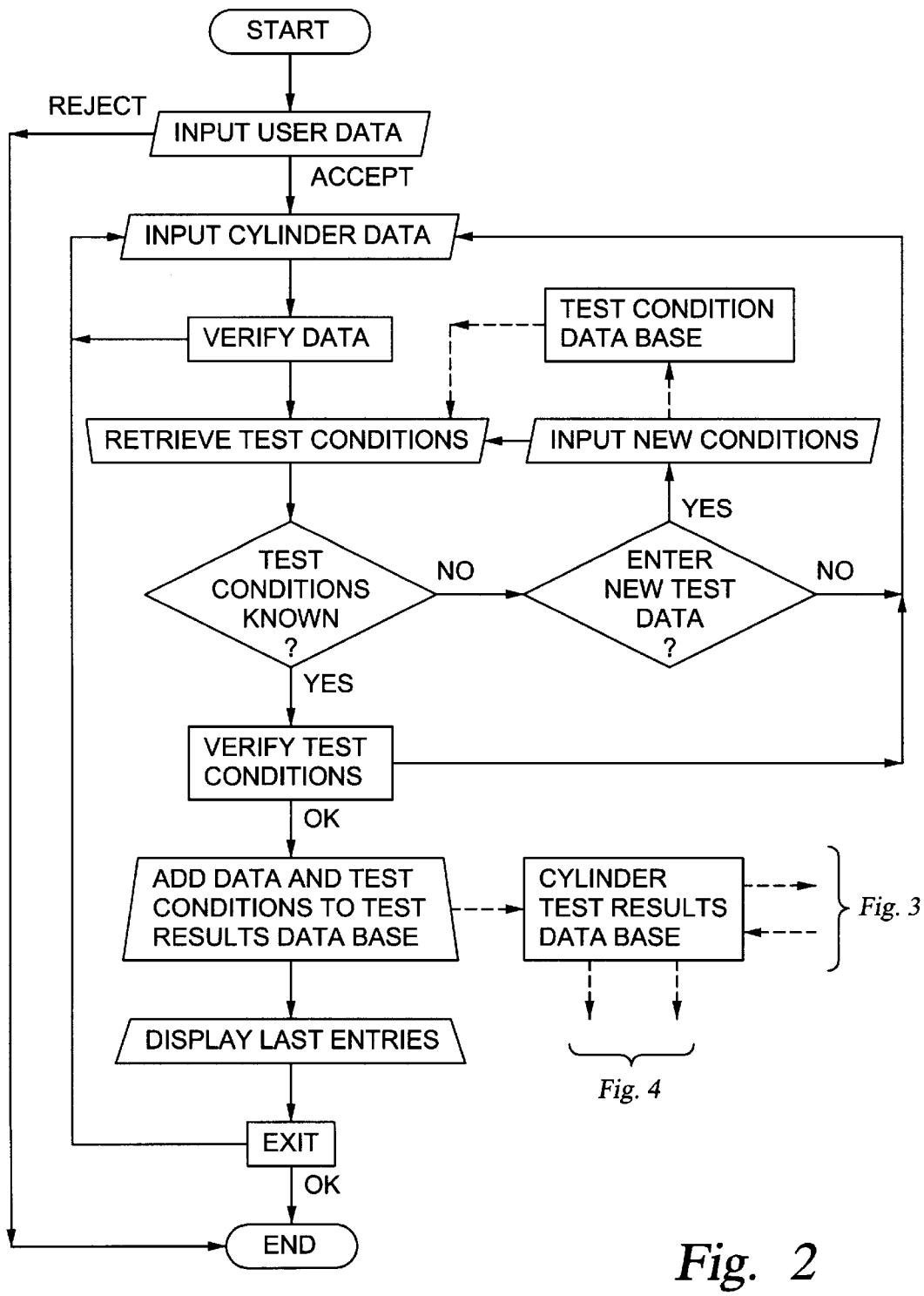
FIGS. 2–4 shows preferred computer program flow charts for the computer controller of FIG. 1.
Figure 3:
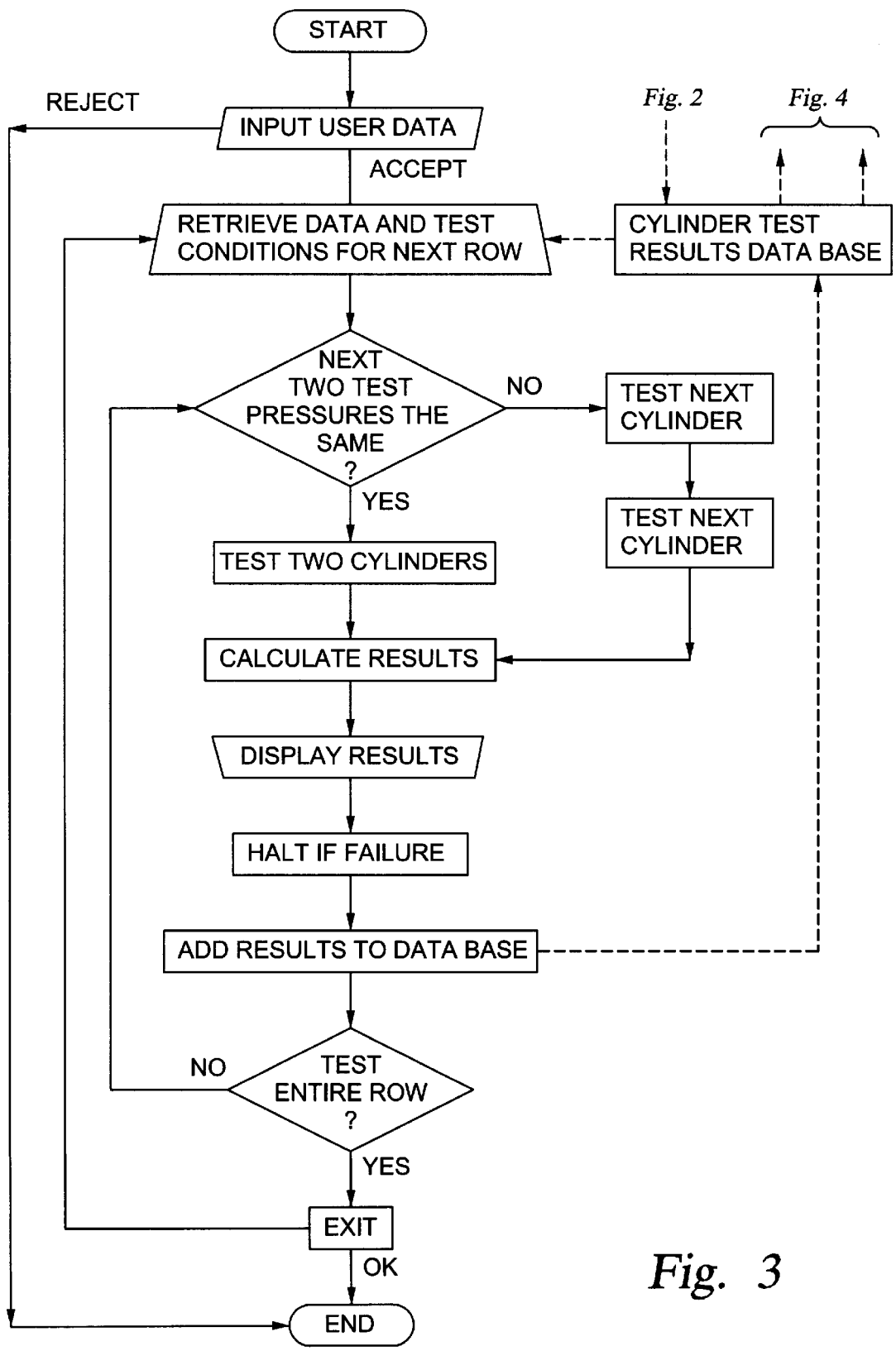

FIG. 2 shows the flow diagrams for cylinder data entry and program interaction with first the test condition database data and then storage of data in the cylinder test database. FIG. 3 shows the flow diagram for operation of the hydrostatic test unit 38. The test operator is not required to enter data during testing but must initially select a test mode unless a default mode is desired. As shown in the diagram, a preferred test mode which uses four test jackets 36 performs dual cylinder testing when the next two cylinders to be tested have the same test pressure. The test unit 38 then operates various control valves to test both cylinders at the same time. The operator can use function keys to remove any of the test jackets 36 from consideration by the program code and to disable dual cylinder testing. Another function key also allows the operator to place the test mode on automatic so that the operator does not have to confirm the start of each test. If a test begins in automatic mode and a cylinder is not detected, the operator receives an error message which must be cleared after the cylinder is loaded.

The test results are calculated and compared to the test conditions to determine whether the cylinder meets both the permanent expansion and the elastic expansion requirements. The program halts whenever a cylinder fails one or more tests and the operator is prompted to mark the cylinder. The operator must then clear the prompt to continue testing cylinders.

Figure 4:
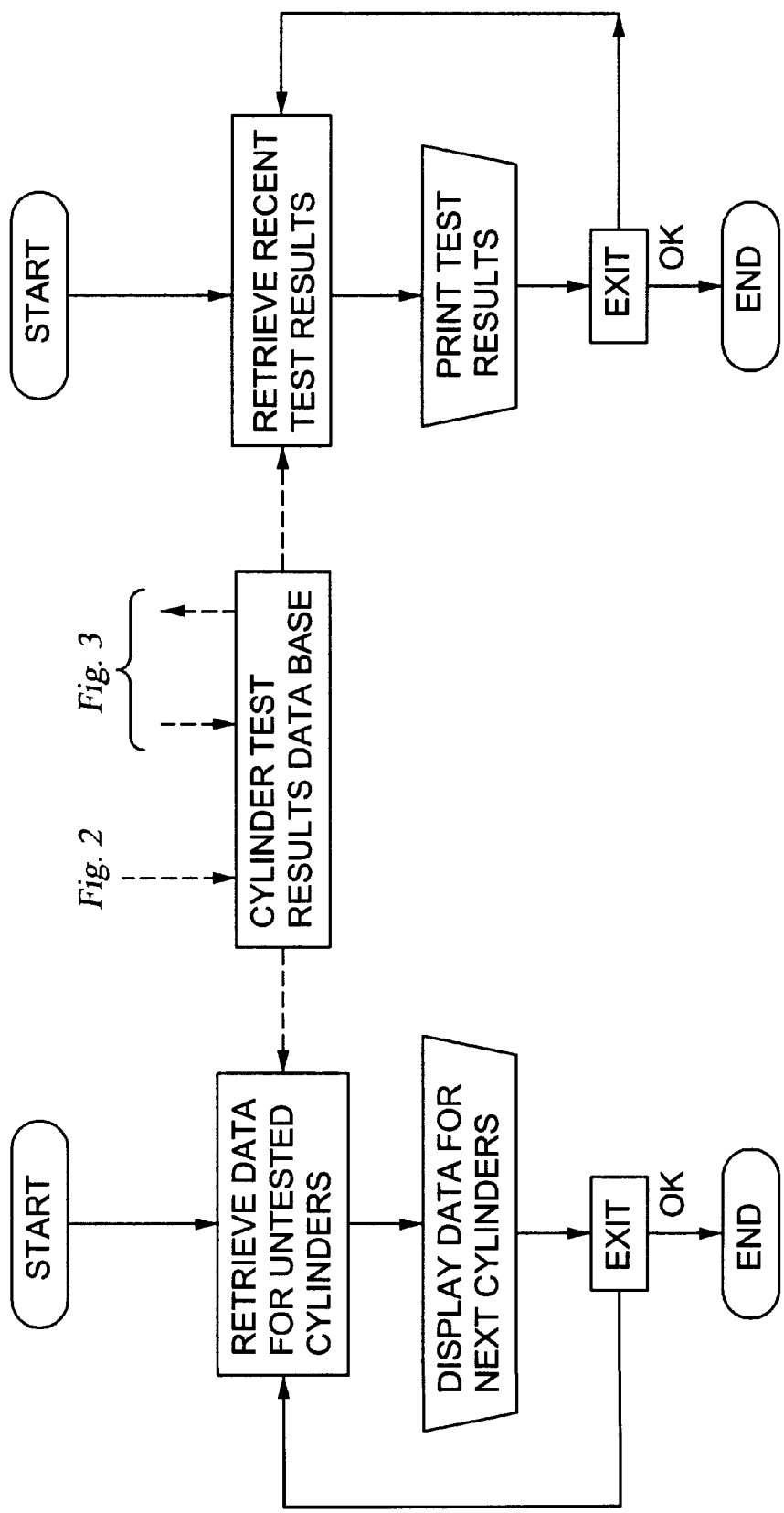

FIG. 4 shows the flow diagrams for additional program code for the apparatus of FIG. 1. The cylinder test results database is accessed by program code for displaying data for each cylinder from the cylinder test database on the monitor 30 at the cylinder staging area 28 prior to hydrostatic testing of the cylinder. The cylinder test results database is also accessed by program code for printing the cylinder test conditions and hydrostatic test results for each cylinder immediately after testing.

The process and apparatus of the invention facilitates testing of gas cylinders by achieving almost continual use of the cylinder test unit which typically sat idle waiting for data entry.

While the foregoing is directed to the preferred embodiment of the present invention, other and further embodiments of the invention may be devised without departing from the basic scope thereof, and the scope thereof is determined by the claims which follow. For examples, the process and apparatus of the invention can be used with ultrasonic testing of the gas cylinders, or the CPU can be replaced by other system controllers which can store and access databases.

What is claimed is:

1. An apparatus for testing of gas cylinders, comprising:
   a cylinder preparation station;
   a cylinder test station;
   a data entry device located near the cylinder preparation station;
   a test control device located near the cylinder test station;
   a computer containing a computer readable program that, when executed, causes one or more controllers to perform the steps of:
      receiving the data entry device for each cylinder;
      selecting test conditions for each cylinder from a cylinder test condition database;
      testing each cylinder using the test conditions;
      prompting marking of each failed cylinder to show which test condition was failed; and
      adding test results to a cylinder test results database.

2. The apparatus of claim 1, wherein the computer readable program code causes the one or more controllers to perform the step of adding the test conditions to the cylinder test results database.

3. The apparatus of claim 2, wherein the computer readable program comprises a cylinder code table which facilitates data entry and selecting the test conditions for each cylinder.

4. The apparatus of claim 3, wherein the cylinder test station comprises one or more hydrostatic test units.

5. The apparatus of claim 4, wherein the computer readable program causes the one or more controllers to test two or more cylinders at the same time at a single test pressure.

6. The apparatus of claim 5, wherein the cylinder code table is updated by the data entry device.

7. The apparatus of claim 6, wherein the one or more controllers comprise one or more CPUs.

8. A process for testing of gas cylinders, comprising the steps of:
   entering data from a cylinder into a data entry device located at a cylinder preparation station;
   selecting test conditions for the cylinder from a cylinder test condition database;
   testing the cylinder at a cylinder test station using the test conditions;
   prompting marking of each failed cylinder to show which test condition was failed; and
   adding test results for the cylinder to a cylinder test results database.

9. The process of claim 8, further comprising the step of adding the test conditions to the cylinder test results database.

10. The process of claim 8, further comprising the steps of selecting a standard cylinder from a cylinder code table.

11. The process of claim 10, further comprising the step of updating the cylinder code table to include additional standard cylinders.

12. The process of claim 8, wherein the cylinder is hydrostatically tested for structural integrity.

13. The process of claim 12, wherein two or more cylinders are tested at the same time at a single test pressure.

14. The process of claim 8, further comprising the steps of cleaning and painting the cylinder.

15. A gas cylinder reconditioning facility, comprising:
   a cylinder preparation station;
   a cylinder test station comprising at least two test units;
   a data entry device located near the cylinder preparation station;
   a test control device located near the cylinder test station; and
   a computer comprising a program that, when executed by a computer, causes one or more controllers to use a cylinder code table to facilitate entering data from each cylinder into the data entry device, select test conditions for each cylinder from a cylinder test condition database, add the test conditions to a cylinder test results database, test each cylinder using the test conditions, prompt marking of each failed cylinder to show which test condition was failed, and add test results to the cylinder test results database.

16. The facility of claim 15, wherein each test unit is a hydrostatic test unit.

17. The facility of claim 16, wherein the program comprises computer readable program code for testing two or more cylinders at the same time at a single test pressure.

18. The facility of claim 17, wherein the cylinder code table is updated by the data entry device.

19. The facility of claim 18, wherein the one or more controllers comprise one or more CPUs.

20. The facility of claim 19, further comprising a cylinder cleaning station.

* * * * *

UNITED STATES PATENT AND TRADEMARK OFFICE
CERTIFICATE OF CORRECTION

PATENT NO : 6,070,451

DATED : June 6, 2000

INVENTOR(S): Hord et al.

It is certified that error appears in the above-identified patent and that said Letters Patent is hereby corrected as shown below:

In column 4, line 10, please replace "test" with "text".

Signed and Sealed this

Twentieth Day of March, 2001

Attest:

NICHOLAS P. GODICI

*Attesting Officer*　　*Acting Director of the United States Patent and Trademark Office*